United States Patent [19]

Tomasula

[11] Patent Number: 5,432,265
[45] Date of Patent: Jul. 11, 1995

[54] PROCESS FOR THE CONTINUOUS REMOVAL OF PRODUCTS FROM HIGH PRESSURE SYSTEMS

[75] Inventor: Peggy M. Tomasula, Titusville, N.J.

[73] Assignee: The United States of America as represented by the Secretary of Agriculture, Washington, D.C.

[21] Appl. No.: 97,182

[22] Filed: Jul. 27, 1993

[51] Int. Cl.⁶ .................. C07K 3/24; F04B 19/12; F04B 37/12; F17D 1/14
[52] U.S. Cl. .................. 530/361; 530/419; 530/420; 422/118; 422/232; 422/242; 422/295; 417/291; 417/315; 137/565
[58] Field of Search .......... 422/118, 232, 242, 295; 530/361, 419, 420; 417/291, 315; 137/565, 207.5, 596

[56] References Cited

U.S. PATENT DOCUMENTS 4,372,918  2/1983  Woods et al. .................. 422/129

OTHER PUBLICATIONS

Karassik "Pump Handbook" pp. 3-47 to 3-63 & 10-124 to 10-128, 1976.
Bloomfield et al., *J. of Dairy Science*, vol. 58, No. 4 pp. 592-601 (1975).
West, David W., *J. of Dairy Research*, vol. 53, pp. 333-352 (1986).
Jordan et al., *NZ Jou. of Dairy Sci. and Tech.*, vol. 22, pp. 247-256 (1987).
Kim et al., *Milchwissenschaft*, vol. 44, pp. 622-625, (1989).
Southward, C. R., *NZ J. of Dairy Sci. and Tech.*, vol. 15, pp. 201-217 (1980).

*Primary Examiner*—William H. Beisner
*Assistant Examiner*—Nancy J. Gromet
*Attorney, Agent, or Firm*—Howard Silverstein; John Fado; Janelle Graeter

[57] ABSTRACT

The continuous removal of solid products from a high-pressure system is achieved by operating a high-pressure pump in reverse to gradually reduce pressure at the exit line to atmospheric pressure. This process allows solid products to exit the system while at the same time maintaining high pressure in the reactor.

12 Claims, 3 Drawing Sheets

PROCESS FOR THE CONTINUOUS REMOVAL OF PRODUCTS FROM HIGH PRESSURE SYSTEMS

BACKGROUND OF THE INVENTION

1. Field of the Invention

Processes for the continuous removal of products from high pressure systems do not currently exist. An effective means of maintaining high pressures in a reaction vessel while at the same time transferring products to atmospheric pressure without interrupting the process or materially reducing particle sizes is not currently known. Supercritical or high pressure processes are therefore usually performed batchwise since the methods are not available for removing the products continuously. For example, the precipitation of proteins and other compounds from solution is a useful separation technique, and high pressure carbon dioxide has been shown to be an effective means of achieving precipitation, but the continuous removal of the precipitated products has not been possible.

This invention relates to a novel process for the continuous removal of products from high pressure systems. In particular, a novel process for the continuous production of proteins by a high pressure carbon dioxide process is disclosed.

2. Description of the Prior Art

It is well known that the addition of acids, such as hydrochloric acid or sulfuric acid, to protein-containing solutions affects pH, thus precipitating any proteins in solution. Other factors such as ionic strength, dielectric properties of the solvent and temperature also affect the solubility of proteins, and these factors can also be taken advantage of for precipitation purposes.

For example, the manufacture of acid casein may occur through the action of lactic acid-producing bacteria or the acidification of skim milk by a mineral acid such as HCl. In either case, acid casein precipitates at the isoelectric point of pH 4.6 and approximately 40° C., conditions at which the negative charges on the surface of the casein micelles are neutralized (Bloomfield and Mead, 1975; West, 1986).

Jordan et al. (1987) have shown that it is possible to precipitate casein by dissolution of carbon dioxide in milk. The reversible reaction for the dissolution of carbon dioxide in water or milk is:

$$CO_2 + H_2O \rightleftharpoons HCO_3^- + H^+$$

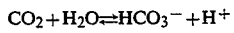

Increasing the pressure of carbon dioxide injected into the milk results in an increased production of $H^+$ thereby lowering pH and causing coagulation of the protein.

Although it is known that proteins are precipitable by $CO_2$ under high pressure, the process has to date been carried out batchwise because of the loss of pressure accompanying the removal of the products, i.e. protein solids. A search has gone on, however, for an effective method of producing proteins continuously so that the machinery involved does not have to go through a shut down/start up cycle, as is required for the precipitation in batches. In addition, high pressure batch processes are slow, impractical and add significantly to the cost of processing, and only small amounts of a product material can be obtained. Casein yields, for example, are only 13% (w/w) of the initial batch liquid on a wet basis.

All high pressure systems reported to date use metering or needle valves to maintain system pressure and remove precipitated or extracted materials after depressurizing the system. Thus neither solid nor liquid components can be effectively removed continuously.

SUMMARY OF THE INVENTION

A process has been discovered which permits the continuous removal of solid products from a high pressure system.

In accordance with this discovery, it is an object of the invention to provide a novel process for the continuous removal of product material from a high pressure system.

It is also an object of the invention to provide a process for the continuous precipitation of and removal of solids from a composition.

DETAILED DESCRIPTION OF THE INVENTION

Figure 1:
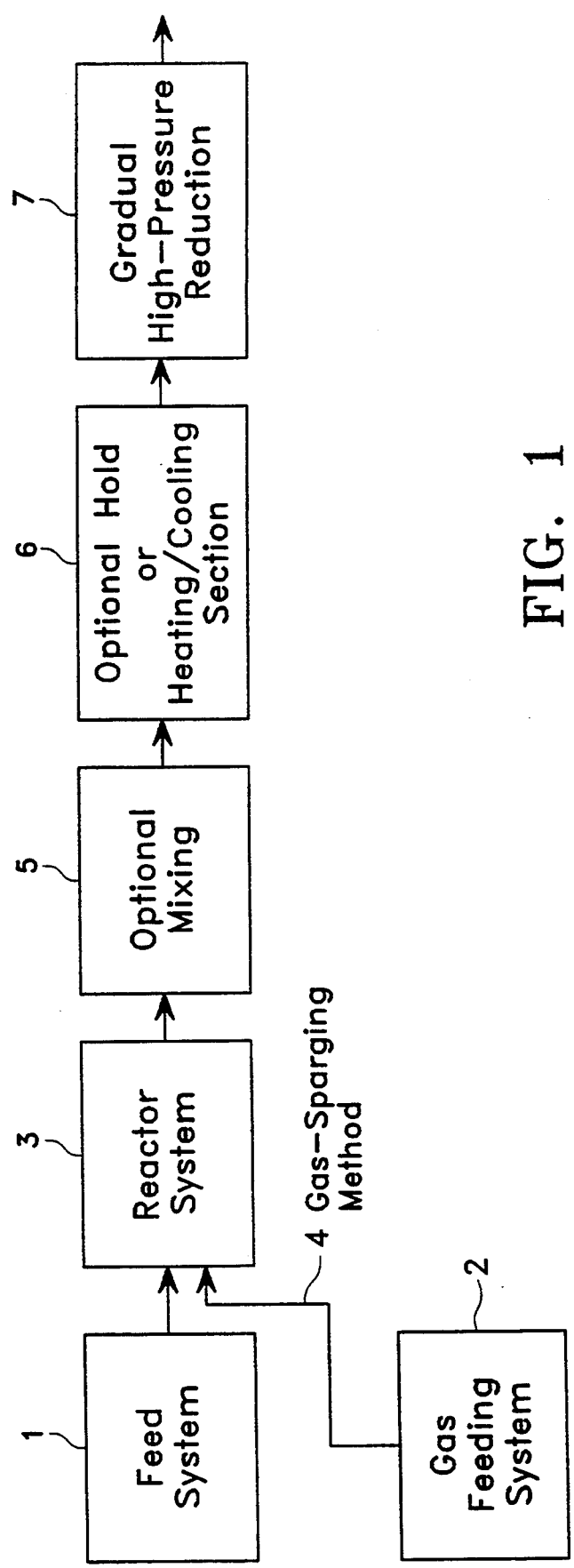
FIG. 1 is a schematic of the general process.

The precipitation process may be used with any reactive gas that lowers or raises pH and results in solids formation. It may also be utilized with other gases to precipitate materials that are known to precipitate in acidic or basic media if the gas forms acid or base solutions.

For example, whole or skim milk contains casein and whey proteins. Casein precipitates from milk optimally in the pH range from about 4.3 to about 5.3 and in the temperature range of about 32° C. to about 60° C. when a mineral acid or lactic acid starter is added to milk. The diameters of the particles may be up to one-half inch or slightly larger, and the precipitate has a cottage cheese-like appearance.

Casein also precipitates when carbon dioxide at pressures greater than about 100 psi are applied to milk. The injection of carbon dioxide into milk causes a drop in pH due to the formation of carbonic acid, the acid product of the reaction between carbon dioxide and water, and causes casein precipitation. Generally, about 20 grams of carbon dioxide is required to initiate casein coagulation in about 500 grams of milk at 38° C. Yield is about 13% of the total product on a wet basis per unit of milk fed into the process. The remaining product is a liquid whey.

Casein is a particularly valuable product, however, any precipitable material may be separated from solution by the novel process described herein. In bacterial fermentation procedures, for example, products, either natural or recombinant, are secreted into fermentation medium, followed by separation from the medium either by precipitation or other means. By utilizing the novel continuous removal process, fermentation medium can be fed from the fermentation apparatus into the high pressure reactor where precipitation occurs, followed by the continuous removal of the precipitated product.

The process is carried out by pumping fluid into a high pressure reactor. The reactor may be cylindrical and constructed of tubing or pipe, although any shape and construction materials are useful so long as they are capable of withstanding the high pressures required by the procedure. Another pump is used to pump liquid $CO_2$, or any other gas, along various locations of the reactor. Alternatively, gas or liquified gas can flow freely into the reactor. The length and diameter of the reactor depend on the amount of material to be processed. The gas and liquid may be preheated or heated in the reactor as the gas-liquid mixture travels along its length.

In a continuous process, the gas must be thoroughly mixed with the liquid, and this may be achieved by vigorous agitation of the flowing liquid. In addition, it is critical that high pressure be maintained.

In order to allow the solid products to exit the system while at the same time maintaining high pressure in the reactor, a high-pressure pump is operated in reverse to gradually reduce pressure at the exit line to atmospheric pressure. The products leaving the high pressure pipe are fed into the discharge end of the pump. The pump may be a progressing cavity pump, an extruder, or any high-pressure pump which can be operated in reverse. A screw pump or filter press may also be used if built to withstand high pressures. The speed of the pump combined with internal clearances sets the line pressure. By utilizing this process, particle size is effectively maintained.

As illustrated by FIG. 1, skim or whole milk, compositions, particulate mixtures, and the like are pumped to the apparatus at room temperature or refrigerated temperature through feed system 1. The system pressure is set by turning on the pump at the discharge side of the pipe 7 and setting it at such a speed as to set the desired operating pressure. Carbon dioxide or other gas is then pumped to the process at slightly below room temperature or fed directly from a cylinder 2, 4 in an amount sufficient to cause precipitation. The gas-liquid mixture in the reactor 3 is heated countercurrently to anywhere from about 35° C. to about 60° C. along the length of the pipe if a double-pipe tubular reactor is used. Alternatively, the gas and liquid streams may be heated to the process temperature and then pumped to the pipe or reactor. The process may be operated from about 100 psi to about 1500 psi, or as required for optimal product. Protein products or methods using this high pressure process may require lower or higher pressures and equipment for handling such. Other processes may be preheated or heated to other temperatures as required.

Figure 2:
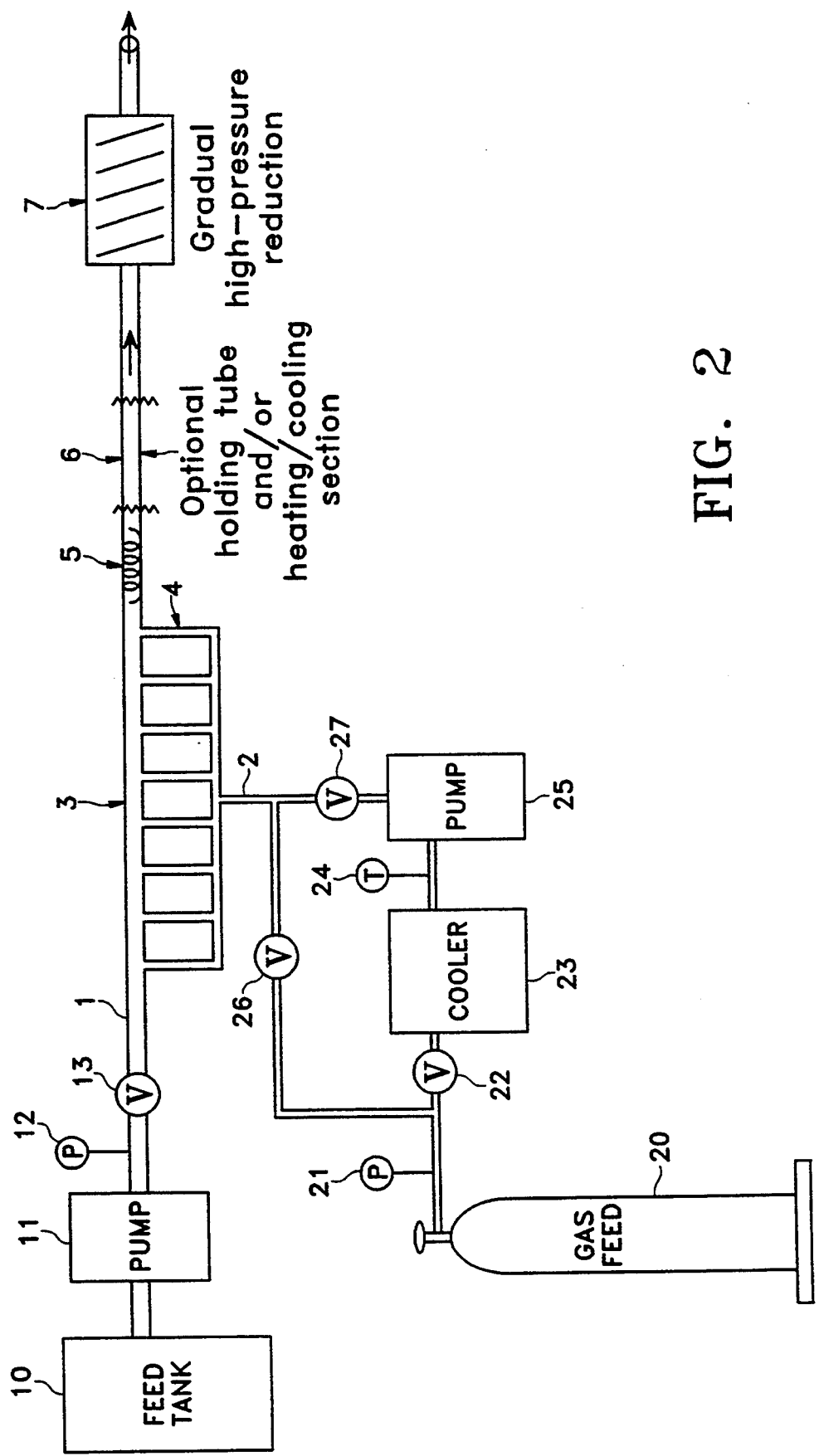
FIG. 2 is a schematic diagram of the continuous high-pressure process apparatus.

FIG. 2 is a schematic diagram of the continuous high-pressure process invention. The feeding section 1 includes feed tank 10, high-pressure pump 11, pressure gauge 12, and check valve 13. The feed tank may be jacketed. The gas feeding section 2 includes gas cylinder 20, which may or may not be equipped with a dip tube, pressure gauge 21, valve 22, cooler 23, thermocouple 24, high pressure pump or compressor 25, valve 26 and check valve 27. Valve 26 is opened and valve 22 is closed if feeding directly from the cylinder. A pressure relief valve is also installed near pump 11.

Mixing section 3 is for contacting the gas/liquified gas and feed. This section is composed of high pressure tubing joined by tees, to allow for sparging from manifold 4. The mixture may move through optional static mixer 5. The mixture, which now may or may not contain solids, moves to 6 where it can optionally be heated or cooled in order to precipitate solids. The section can also include an optional holding tube to increase residence time. The mixture is then removed by the reversed high pressure pump 7.

To operate the continuous high-pressure process for the production of casein, milk heated to the system temperature is pumped from feed tank 10, mixed at sections 3 and 5, and pumped through the reactor and holding tube 6. Pump 7 is adjusted to an rpm that does not allow pressure buildup in the line. Once the internal parts of the pump are wetted, the pump speed is reduced so that line pressure builds.

Line pressure may range from about 400 to about 1500 psi. Liquified $CO_2$ in cylinder 20 is fed through valve 22, through cooler 23 if there is possibility of gas flashing, through pump 25, through manifold 4 and to section 3. Valve 26 is closed. Alternatively, valve 22 may be closed and the gas fed directly through valve 26.

The horizontal reactor 3 may be constructed of heavy-walled tubing or pipe to accommodate a desired throughput, reactant contacting pattern, and residence time.

Figure 3:
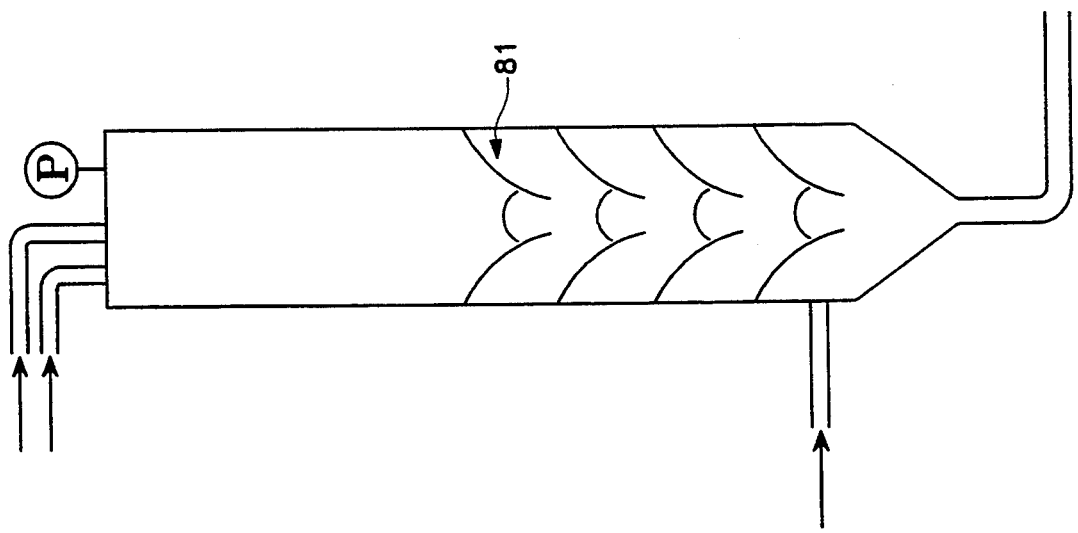
FIG. 3 shows a vertical column which may be used to replace reactor system 3 as shown in FIGS. 1 and 2.

Reactor system 3 may be replaced by a vertical column constructed of stainless steel, as shown in FIG. 3, and operated as described previously.

FIG. 3 depicts a vertical column with diameter 5–10 times the feed line and equipped with 4 internal trays 81 to slow the movement of the particles. The trays may be of any design. Flat plates with slots cut to accommodate particle size may be installed, or as illustrated, cone shaped trays with overhead domes to slow movement of precipitate or solids through the column. For the casein process, the column may be top fed with milk while $CO_2$ at 31° C. and 400–800 psi enters the bottom.

The invention may be used as described by the dairy industry for the removal of casein from milk. Many other uses, however, are also contemplated. It is applicable, for example, to food, pharmaceutical and chemical industries which currently use mineral acids or bases to precipitate proteins or other compounds from solution. It can be used to precipitate any substances which are known to precipitate in acidic media, including such natural materials as blood proteins, carbohydrates, tannins, pectins and the like.

The invention may also be utilized to remove suspended solids from a high pressure system without deforming or breaking the solids. For example, solids which are cleaned in acid or base solutions may be fed through the system by feeding the solids suspended in water or slurries through a feed system which is a modification of feed system 1 of FIGS. 1 and 2. In this embodiment, feed system 1 is replaced by a hopper feed system, feed valve, pump or a similar feed system which can accommodate a slurry or solids. This modification is required in instances where slurries or any solids-containing liquid is involved.

This process may be used to continuously sterilize juices or other liquids that contain suspended deformable solids. In addition, the system may also be used in sterilization processes for fresh spices or for meat, chicken or vegetable pieces, puffed pieces and the like.

This invention is also useful in the food industry for the preparation of canned or otherwise packaged pre-prepared foods such as soups, stews, sauces or any foods which may be cooked under pressure. In addition, the system is also useful as part of a process for making soft cheeses such as mozzarella or cottage cheeses. In this application, gas feeding system 2 is replaced by a steam feed or eliminated altogether if heating is external.

The system may also be used for supercritical extraction where the solids containing the extractable material move through the process along with the carbon dioxide or other gas which is supplied to the system at pressure and temperature greater than critical. The solids enter the process through a hopper or screw pump. Extraction would occur in 3 of FIG. 2 and the tube or pipe length or diameter would be chosen based on desired residence time, desired throughput, and percent of suspended solids. The mixture would enter a separation system at the discharge end of the pipe where the extract mixture is passed through a valve, and the extract and gas separated as in conventional processes. The solids would be removed as described above using the pressure reduction system. This invention presents an alternative process for the extraction of cholesterol from animal products, the removal of oils from seeds, and the like. Following removal from the system, the solid products may be further separated as necessary by conventional means, such as settling, centrifugation, absorption or the like.

The following Example is intended only to further illustrate the invention and is not intended to limit the scope of the invention which is defined by the claims.

EXAMPLE

Continuous Casein Production Using High-pressure Carbon Dioxide in a Double-pipe Tubular Reactor Milk and carbon dioxide were fed to the reactor system. This system consisted of a double-pipe tubular reactor. Milk at 3° C. was pumped from the feed tank to a section of the high pressure tubing. Liquid carbon dioxide at 6° C. was pumped into the flowing milk stream at five points along the tube using a packed plunger liquid end pump. A static mixer at the end of this section facilitated mixing. The temperature of the reactor was controlled at 40° C. by hot water flowing countercurrently to the milk-carbon dioxide stream. The residence time of the reactor was 1 minute. Flow rates of milk and carbon dioxide were approximately 55 kg/hr and 2 kg/hr respectively. A progressing cavity pump fed through the discharge end and operated in reverse was used to pump the casein and whey from the high-pressure conditions at 1000 psi down to atmospheric pressure.

A friable casein coagulum was obtained with a calcium content greater than acid-precipitated casein. The corresponding whey had a lower calcium content than whey from an acid-precipitation process and a pH of 6.3.

The foregoing detailed description is given merely by way of illustration and modifications and variations may be made therein without departing from the spirit and scope of the invention.

INDEX OF APARATUS ELEMENTS DESIGNATED BY A NUMERAL

1 Feeding section
2 Gas feeding section
3 Mixing section
4 Manifold
5 Optional static mixer
6 Optional holding tube and/or heating/cooling section
7 Reversed high pressure pump
10 Feed tank
11 High pressure pump
12 Pressure gauge
13 Check valve
20 Gas cylinder
21 Pressure gauge
22 Valve
23 Cooler
24 Thermocouple
25 High pressure pump or compressor
26 Valve
27 Check valve

I claim:

1. A process for the continuous production and removal of products from a high pressure system comprising an inlet line, a high pressure pump associated with said inlet line, a high pressure reactor, and an outlet line, and a high pressure pump associated with said outlet line, said process comprising
    a) pumping a fluid into the high pressure reactor by means of said high pressure pump associated with said inlet line,
    b) applying a high-pressure treatment to the fluid to obtain the products,
    c) removing the product-containing treated fluid from the high pressure system by feeding said treated fluid into the discharge end of said high-pressure pump associated with said outlet line and operating said high-pressure pump associated with said outlet line in reverse in order to gradually reduce fluid pressure to atmospheric pressure.

2. The process of claim 1, wherein said fluid is a slurry.

3. The process of claim 1, wherein said high-pressure treatment comprises mixing the fluid with gas.

4. The process of claim 3, wherein said gas is carbon dioxide.

5. The process of claim 3, wherein said gas is liquified.

6. The process of claim 1, wherein said high pressure treatment is from about 100 psi to about 1500 psi.

7. The process of claim 1, wherein said high-pressure treatment additionally comprises heating the fluid.

8. The process of claim 1, wherein said high-pressure pump associated with said outlet line is any high-pressure pump which can be operated in reverse.

9. The process of claim 1, wherein said high-pressure pump associated with said outlet line is a progressing cavity pump.

10. The process of claim 1, wherein said products are protein.

11. The process of claim 10, where said protein is casein.

12. The process of claim 11, wherein said fluid is heated to temperatures of about 35° C. to about 60° C.

* * * * *